(12) United States Patent
Yokozeki (10) Patent No.: US 6,582,373 B2
(45) Date of Patent: Jun. 24, 2003

(54) AUTOMATIC BLOOD-PRESSURE MEASURING APPARATUS

(75) Inventor: Akihiro Yokozeki, Komaki (JP)

(73) Assignee: Colin Corporation, Komaki (JP)

( * ) Notice: Subject to any disclaimer, the term of this patent is extended or adjusted under 35 U.S.C. 154(b) by 0 days.

(21) Appl. No.: 09/955,194

(22) Filed: Sep. 19, 2001

(65) Prior Publication Data

US 2002/0052555 A1 May 2, 2002

(30) Foreign Application Priority Data

Oct. 30, 2000 (JP) ........................................ 2000-330593

(51) Int. Cl.⁷ ................................................ A61B 5/02
(52) U.S. Cl. ........................ 600/493; 600/490; 600/485
(58) Field of Search ................................ 600/485–490, 600/491–494, 495

(56) References Cited

U.S. PATENT DOCUMENTS 4,295,471 A * 10/1981 Kaspari ........................ 600/488
4,729,382 A * 3/1988 Schaffer et al. ............. 600/492
6,106,478 A * 8/2000 Tochikubo et al. .......... 600/494

FOREIGN PATENT DOCUMENTS

| JP | 1-256930 | 10/1989 |
| JP | 5-168601 | 7/1993 |
| JP | 2-2702297 | 10/1997 |
| JP | 2001-333889 A | 12/2001 |

* cited by examiner

Primary Examiner—Robert L. Nasser
Assistant Examiner—Patricia C. Mallari
(74) Attorney, Agent, or Firm—Oliff & Berridge, PLC (57) ABSTRACT

An apparatus for automatically measuring a blood pressure of a living subject, including an inflatable cuff which is adapted to be wound around a portion of the subject, an increase-end-pressure determining device for determining, based on a cuff pulse wave occurring to the cuff when a pressure in the cuff is increased at a first rate, an increase-end pressure to which the pressure of the cuff is increased at the first rate, at which the increasing of the pressure of the cuff is ended, and from which the pressure of the cuff is decreased at a second rate lower than the first rate, and a blood-pressure determining device for determining a blood pressure of the subject based on a physical signal obtained from the subject when the pressure of the cuff is decreased at the second rate from the increase-end pressure.

7 Claims, 6 Drawing Sheets

AUTOMATIC BLOOD-PRESSURE MEASURING APPARATUS

BACKGROUND OF THE INVENTION

1. Field of the Invention

The present invention relates to an automatic blood-pressure measuring apparatus which automatically measures a blood pressure of a living subject based on a physical signal obtained when a pressure in a cuff is decreased.

2. Related Art Statement

There is known an automatic blood-pressure measuring apparatus of a type which includes a cuff inflatable to press a portion of a living subject and measures a blood pressure of the subject based on a physical signal, such as a pulse wave or Korotkoff sounds, that is continuously obtained when the pressure of the cuff is slowly decreased.

The pressure of the cuff needs to be increased, in advance, before the cuff pressure is slowly decreased. It is the most appropriate for the increasing of the cuff pressure to be stopped at the lowest possible pressure at which, however, the cuff can completely stop the flow of blood through the portion of the subject around which the cuff is wound. The lowest possible pressure needs to be higher than a systolic blood pressure of the subject.

However, individual living subjects may have different systolic blood-pressure values. Hence, the conventional automatic blood-pressure measuring apparatus quickly increases the pressure of the cuff up to a prescribed increase-end pressure (e.g., 180 mmHg) that is sufficiently higher than an average systolic blood pressure. However, for some subjects, the prescribed increase-end pressure may be too low to measure their systolic blood-pressure values. In addition, for other subjects, the prescribed increase-end pressure may be unnecessarily high to measure their systolic blood-pressure values, causing them to feel discomfort because the high pressure of the cuff is applied in an unnecessarily long time.

SUMMARY OF THE INVENTION

It is therefore an object of the present invention to provide an automatic blood-pressure measuring apparatus which automatically measures a blood pressure of a living subject based on a physical signal obtained when a pressure in a cuff is decreased after having been increased to an increase-end pressure and which can increase the cuff pressure to the increase-end pressure appropriate for a systolic blood pressure of the subject.

The above object has been achieved by the present invention. According to the present invention, there is provided an apparatus for automatically measuring a blood pressure of a living subject, comprising an inflatable cuff which is adapted to be wound around a portion of the subject; an increase-end-pressure determining means for determining, based on a cuff pulse wave occurring to the cuff when a pressure in the cuff is increased at a first rate, an increase-end pressure to which the pressure of the cuff is increased at the first rate, at which the increasing of the pressure of the cuff is ended, and from which the pressure of the cuff is decreased at a second rate lower than the first rate; and a blood-pressure determining means for determining a blood pressure of the subject based on a physical signal obtained from the subject when the pressure of the cuff is decreased at the second rate from the increase-end pressure.

According to this invention, the increase-end-pressure determining means determines, based on a cuff pulse wave occurring to the cuff when the pressure of the cuff is increased at a first rate, an increase-end pressure at which the increasing of the pressure of the cuff is ended. Since a waveform of the cuff pulse wave occurring to the cuff when the cuff pressure is increased changes according to a relationship between cuff pressure and subject's blood pressure, the thus determined increase-end pressure is appropriate for the subject whose systolic blood pressure may differ from those of other subjects.

Preferably, the increase-end-pressure determining means determines the increase-end pressure based on a rate of decrease of an after-peak-point portion of at least one heartbeat-synchronous pulse of the cuff pulse wave occurring to the cuff when the pressure of the cuff is increased at the first rate, the after-peak-point portion starting with a peak point of the heartbeat-synchronous pulse.

The respective decrease rates of respective after-peak-point portions of respective heartbeat-synchronous pulses of the cuff pulse wave increase as the pressure of the cuff is increased in a range lower than a systolic blood pressure of the subject, and largely decrease as the cuff pressure is increased over the systolic blood pressure. Therefore, the increase-end-pressure determining means may determine the increase-end pressure based on a pressure of the cuff when one of the respective decrease rates of respective after-peak-point portions of respective pulses of the cuff pulse wave significantly largely decreases, or may determine, as the increase-end pressure, a pressure greater by a prescribed additional pressure than a pressure of the cuff when one of the respective decrease rates of the respective after-peak-point portions is greater than a prescribed decrease-rate value.

Preferably, the increase-end-pressure determining means determines the increase-end pressure based on whether a peak portion of at least one heartbeat-synchronous pulse of the cuff pulse wave occurring to the cuff when the pressure of the cuff is increased at the first rate has a small-projection shape.

In the state in which the cuff completely stops the flow of blood through the portion of the subject around which the cuff is wound, the peak portion of each heartbeat-synchronous pulse of the cuff pulse wave occurring to the cuff has a small-projection shape. Therefore, the increase-end-pressure determining means can determine the increase-end pressure based on whether the peak portion of one heartbeat-synchronous pulse of the cuff pulse wave has the small-projection shape.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF PREFERRED EMBODIMENTS

Figure 1:
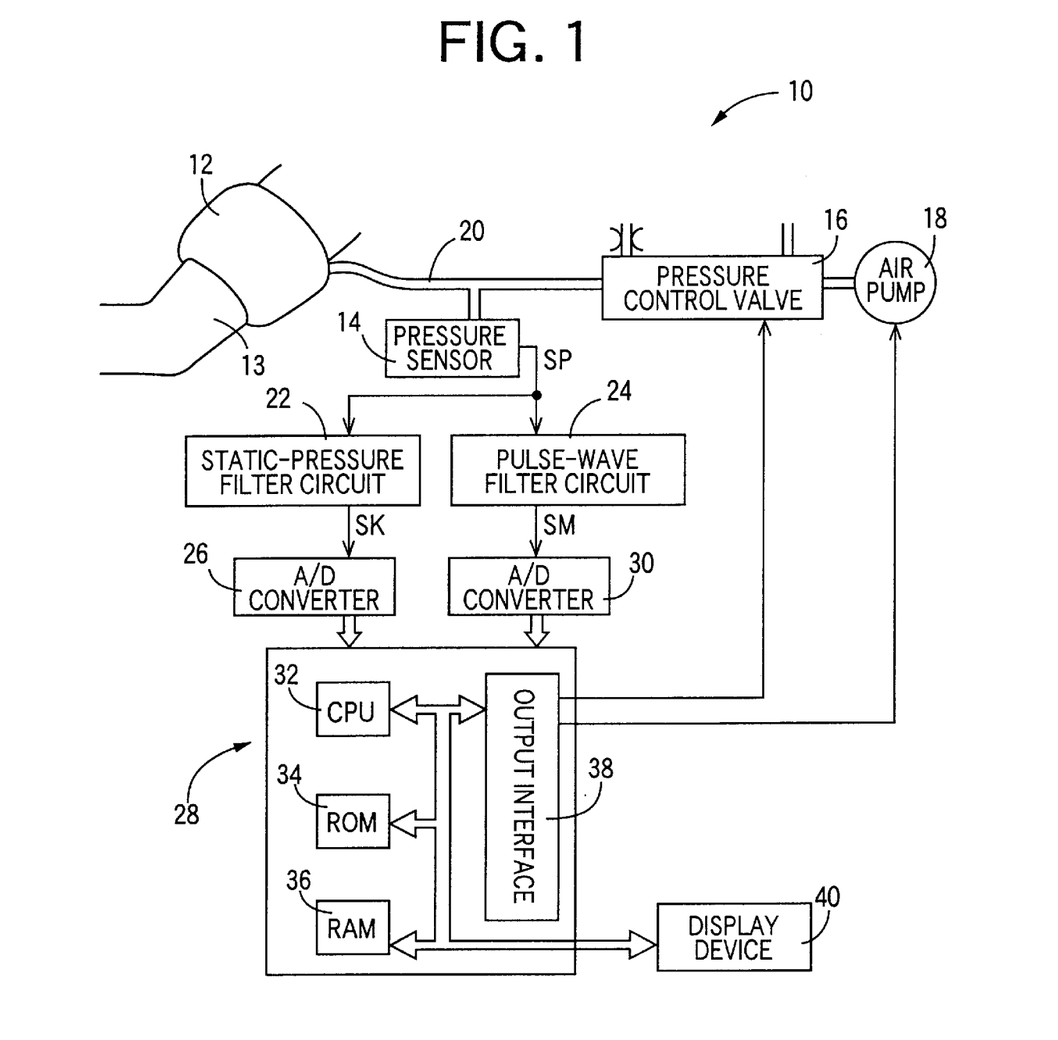
FIG. 1 is a diagrammatic view for explaining a construction of an automatic blood-pressure measuring apparatus to which the present invention is applied.

Hereinafter, there will be described an embodiment of the present invention in detail by reference to the accompanying drawings. FIG. 1 shows a diagrammatic view for explaining a construction of an automatic blood-pressure measuring apparatus 10 to which the present invention is applied.

In FIG. 1, the blood-pressure measuring apparatus 10 includes a cuff 12 which has a belt-like cloth bag and a rubber bag accommodated in the cloth bag and which is adapted to be wound around, e.g., an upper arm 13 of a living subject. The cuff 12 is connected to a pressure sensor 14, a pressure control valve 16, and an air pump 18 via a piping 20. The pressure control valve 16 is selectively placed in a pressure-supply position in which the control valve 16 permits a pressurized air to be supplied from the air pump 18 to the cuff 12, a slow-deflation position in which the control valve 16 allows the pressurized air to be slowly discharged from the cuff 12, and a quick-deflation position in which the control valve 16 permits the pressurized air to be quickly discharged from the cuff 12.

The pressure sensor 16 detects an air pressure $P_T$ in the cuff 10, and supplies a pressure signal SP representing the detected pressure, to each of a static-pressure filter circuit 22 and a pulse-wave filter circuit 24. The static-pressure filter circuit 22 includes a low-pass filter and extracts, from the pressure signal SP, a static-pressure component $P_C$ contained in the signal SP, i.e., a static-pressure signal SK representing the static pressure $P_C$ in the cuff 10. The static-pressure signal SK is supplied to a control device 28 via an analog-to-digital (A/D) converter 26. The pulse-wave filter circuit 24 includes a band-pass filter and extracts, from the pressure signal SP, an oscillating component having predetermined frequencies, i.e., a pulse-wave signal SM. The pulse-wave signal $SM_1$ is supplied to the control device 28 via an A/D converter 30. The pulse-wave signal SM represents a cuff pulse wave $W_C$, i.e., a pressure pulse wave which is produced from a brachial artery, not shown, of the patient in synchronism with the heartbeat of the patient and is propagated to the cuff 12.

The control device 28 is provided by a so-called microcomputer including a central processing unit (CPU) 32, a read only memory (ROM) 34, a random access memory (RAM) 36, and an output interface 38, etc. The CPU 32 processes signals according to the control programs prestored in the ROM 34 by utilizing the temporary-storage function of the RAM 36, and supplies drive signals via the output interface 38 to respective drive circuits, not shown, associated with the pressure control valve 16 and the air pump 18 so as to change the pressure in the cuff 12 and determine a blood pressure BP of the patient based on the static-pressure signal SK and the pulse-wave signal SM obtained during the changing of the pressure in the cuff 12. In addition, the CPU 32 operates a display device 40 to display the thus determined blood pressure BP. The display device 48 may include a cathode ray tube (CRT).

Figure 2:
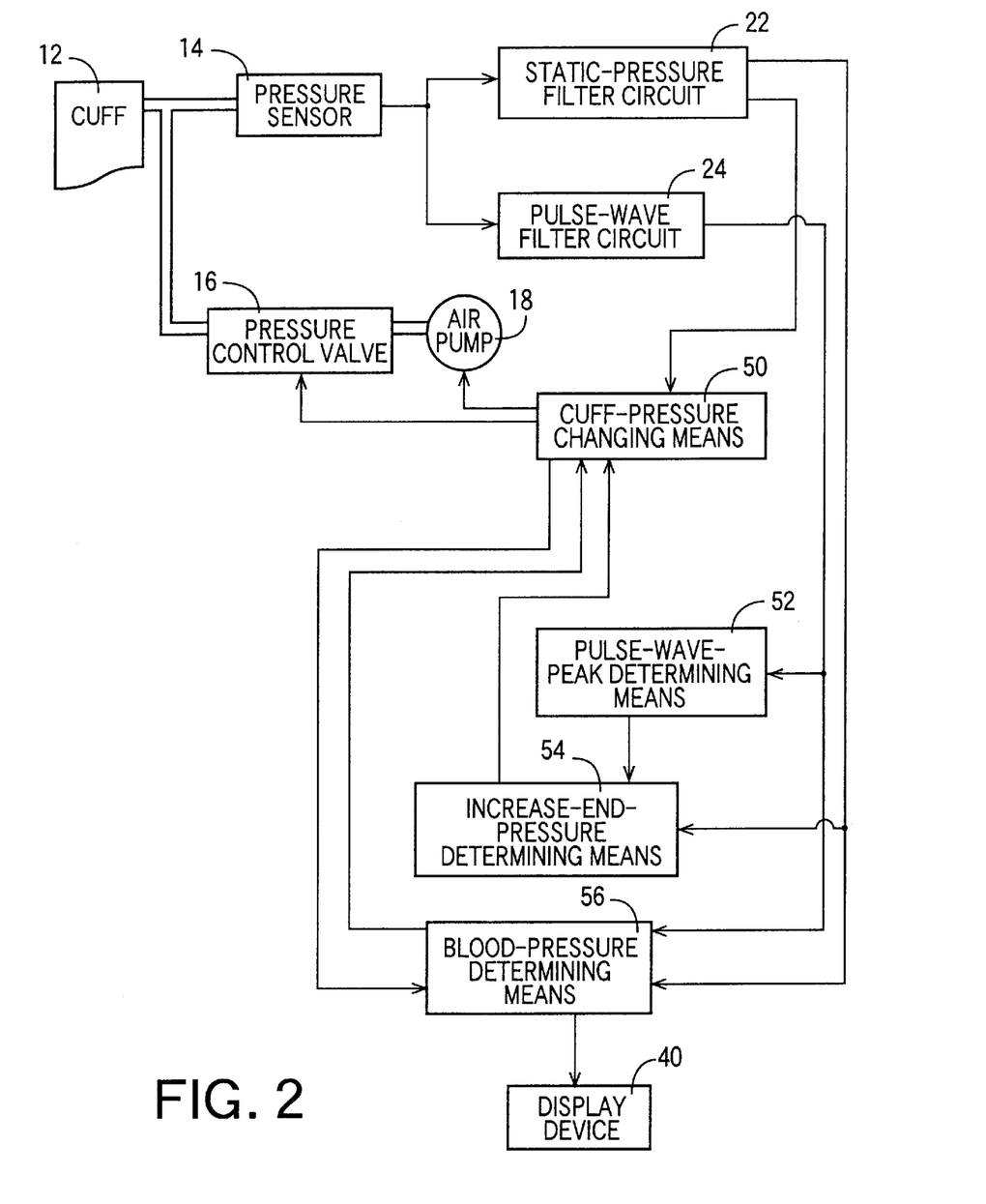
FIG. 2 is a block diagram for explaining essential functions of a control device of the apparatus of FIG. 1.

FIG. 2 is a block diagram for explaining essential functions of the control device 28. In the figure, a cuff-pressure changing means 50 operates the pressure control valve 16 and the air pump 18, recognizes the static pressure $P_C$ based on the static-pressure signal SK supplied from the static-pressure filter circuit 22, quickly increases the static pressure $P_C$ at a prescribed high rate (e.g., from 30 to 50 mmHg/sec), up to an increase-end pressure $P_{CE}$, determined by an increase-end-pressure determining means 54 described below, and subsequently slowly decreases the static pressure $P_C$ at a prescribed low rate (e.g., 3 mmHg/sec). After a blood-pressure determining means 56, described below, determines a blood pressure BP, the changing means 50 quickly decreases the static pressure $P_C$.

A pulse-wave-peak determining means 52 successively determines, based on the pulse-wave signal SM continuously supplied thereto when the static pressure $P_C$ is quickly increased by the cuff-pressure changing means 50, respective peak points of successive heartbeat-synchronous pulses of the cuff pulse wave $W_C$ continuously detected during the quick increase of the static pressure $P_C$.

An increase-end-pressure determining means 54 determines, based on a shape of the cuff pulse wave $W_C$, an increase-end pressure $P_{CE}$ at which the quick increase of the static pressure $P_C$ by the cuff-pressure changing means 50 is ended. When the shape of the cuff pulse wave $W_C$ detected during the change of the static pressure $P_C$ was studied in detail, it was found that the shape of the cuff pulse wave $W_C$ changes depending upon the relationship between the static pressure $P_C$ and the blood pressure BP of the subject. According this finding, the increase-end-pressure determining means 54 determines the increase-end pressure $P_{CE}$, based on the shape of the cuff pulse wave $W_C$, in a manner described below in detail.

Figure 3:
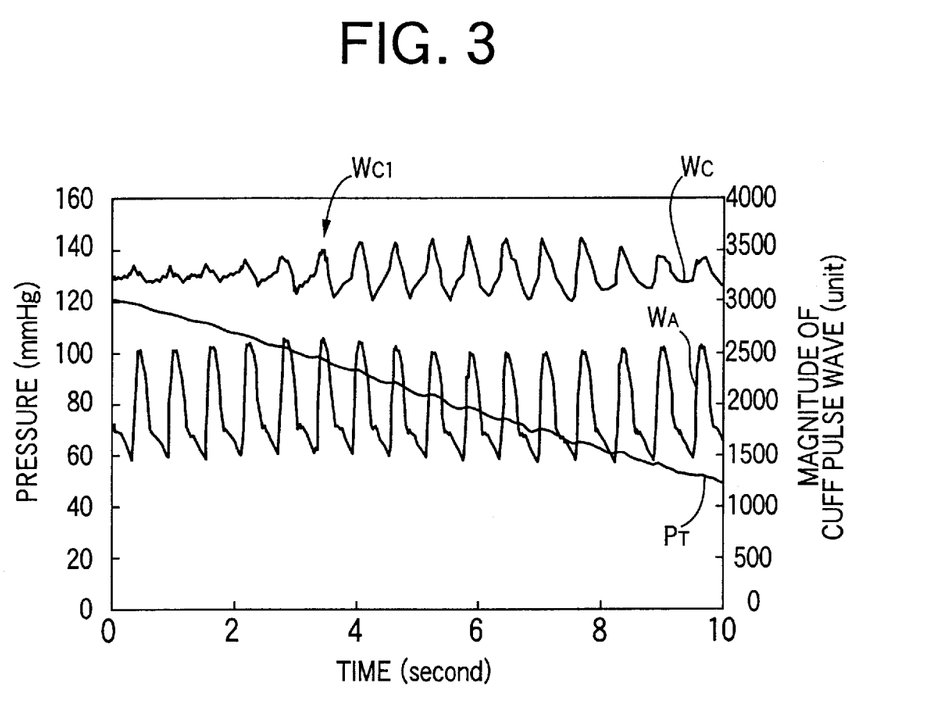
FIG. 3 is a graph showing, along a common time axis, a cuff pressure $P_T$ detected when a static pressure $P_C$ is slowly decreased by a cuff-pressure changing means shown in FIG. 2; a cuff pulse wave $W_C$ contained in the cuff pressure $P_T$, and a blood-pressure waveform $W_A$ measured through a catheter during the slow pressure decreasing.

FIG. 3 is a graph showing, along a common time axis, the cuff pressure $P_T$ represented by the pressure signal SP produced when the static pressure $P_C$ is slowly decreased by the cuff-pressure changing means 50; the cuff pulse wave $W_C$ contained in the cuff pressure $P_T$; and a blood-pressure waveform $W_A$ representing the change of intraarterial blood pressure of the other arm than the arm around which the cuff 12 is wound. The intraarterial blood-pressure waveform $W_A$ is measured in a direct method (so-called "A-LINE" method) using a catheter inserted in an artery, during the slow decreasing of the static pressure $P_C$. The cuff pulse wave $W_C$ shown in FIG. 3 is a differentiated curve.

In FIG. 3, each of respective peak points of successive heartbeat-synchronous pulses of the blood-pressure waveform $W_A$ measured using the catheter represents a systolic blood pressure $BP_{SYS}$ of the subject. Therefore, the sixth heartbeat-synchronous pulse $W_{C1}$ of the cuff pulse wave $W_C$, counted from the left-hand end of the graph, is the first pulse detected after the cuff pressure $P_T$ is decreased down to a value lower than the systolic blood pressure $BP_{SYS}$. When, for each of the heartbeat-synchronous pulses of the cuff pulse wave $W_C$, a rate of decrease V of an after-peak-point portion of the each pulse detected during a prescribed time duration $T_1$ shorter than a time duration from a peak point of the each pulse to a rising point of another pulse following the each pulse, that is, a slope of a straight line connecting between the peak point of the each pulse and another point of the each pulse detected after the prescribed time duration $T_1$ and before the rising point of the following pulse is determined, the respective determined decrease rates V of the pulses of the cuff pulse wave $W_C$ detected after the sixth pulse $W_{C1}$ decrease as the cuff pressure $P_T$ decreases. Meanwhile, the respective determined decrease rates V of the pulses detected before the sixth pulse $W_{C1}$, i.e., in the state in which the flow of blood through the upper arm 13 is stopped by the cuff 12, are much lower than the decrease rate V of any pulse detected after the sixth pulse $W_{C1}$ is detected and when the cuff pressure $P_T$ is lower than, and near to, the systolic blood pressure $BP_{SYS}$. In addition, a peak portion of each of the first to fourth pulses of the cuff pulse wave $W_C$ detected in the state in which the flow of blood through the upper arm 13 is stopped by the cuff 12, has a small-projection shape. Here, the peak portion of each pulse is defined as a portion of the each pulse that includes, as a center of the peak portion, a peak point of the each pulse and has a length not longer than an entire length of the ease pulse, e.g., equal to half the entire length. The small-projection shape means that the peak portion projects like a small projection around the peak point as the center thereof.

Although the graph shown in FIG. 3 is obtained when the cuff pressure $P_T$ is slowly decreased, a similar graph representing a relationship among the shape of cuff pulse wave $W_C$, the cuff pressure $P_T$, and the decrease rate V can be obtained when the cuff pressure $P_T$ is increased. More specifically described, the respective decrease rates V of the pulses of the cuff pulse wave $W_C$ increase as the cuff pressure $P_T$ is increased below the systolic blood pressure $BP_{SYS}$. Meanwhile, the respective decrease rates V of the pulses of the cuff pulse wave $W_C$ largely decrease as the cuff pressure $P_T$ is increased above the systolic blood pressure $BP_{SYS}$. Also when the cuff pressure $P_T$ is increased, the respective peak portions of the pulses of the cuff pulse wave $W_C$ detected in the state in which the blood flow is stopped takes a small-projection shape.

Thus, the increase-end-pressure determining means 54 determines, based on the respective peak points of the heartbeat-synchronous pulses of the cuff pulse wave $W_C$ determined by the pulse-wave-peak determining means 52, the respective decrease rates V of the respective pulses of the cuff pulse wave $W_C$, and determines an increase-end pressure $P_{CE}$ based on a fact that one of the respective decrease rates V is greater than a prescribed reference value $V_{SET}$ (>0), or a fact that a change value (e.g., a rate of change, or an amount of change) of one of the respective decrease rates V is negative. The determining means 54 determines one increase-end pressure $P_{CE}$, each time the pressure of cuff 12 is increased to stop the blood flow in the upper arm 13 and measure a blood pressure BP of the subject. Alternatively, the increase-end-pressure determining means 54 determines, based on the respective peak points of the heartbeat-synchronous pulses of the cuff pulse wave $W_C$ determined by the pulse-wave-peak determining means 52, the respective peak portions of the respective pulses of the cuff pulse wave $W_C$, and determines an increase-end pressure $P_{CE}$ based on a fact that one of the respective peak portions has a small-projection shape. In the latter case, too, the determining means 54 determines one increase-end pressure $P_{CE}$ each time the pressure of cuff 12 is increased. The above-mentioned reference value $V_{SET}$ is experimentally determined, in advance, such that the reference value $V_{SET}$ is equal to a decrease rate V of the pulse of the cuff pulse wave $W_C$ detected in the state in which the static pressure $P_C$ is equal to a systolic blood pressure.

A blood-pressure determining means 56 determines, based on the static-pressure signal SK and the pulse-wave signal SM supplied from the static-pressure filter circuit 22 and the pulse-wave filter circuit 24 when the static pressure $P_C$ is slowly decreased by the cuff-pressure changing means 50, a systolic blood pressure $BP_{SYS}$, a mean blood pressure $BP_{MEAN}$, and a diastolic blood pressure $BP_{DIA}$ of the subject, according to well-known oscillometric algorithm, and operates the display device 40 to display the thus determined blood pressure values $BP_{SYS}$, etc.

Next, there will be described the operation of the control device 28, by reference to the flow chart shown in FIG. 4. In the control routine represented by the flow chart, first, at Step SA1 (hereinafter, "Step" is omitted, if appropriate), the control device 28 judges whether a start switch, not shown, has been operated by an operator, e.g., a medical staff. SA1 is repeated till a positive judgment is made.

Meanwhile, if a positive judgment is made at SA1, the control proceeds with SA2 to switch the pressure control valve 16 to its pressure-supply position and operate the air pump 18, so that the static pressure $P_C$ of the cuff 12 is quickly increased at a prescribed rate (e.g., 40 mmHg/sec).

Then, at SA3, the control device 28 judges whether the control device 28 has received, during the increasing of the static pressure $P_C$ started at SA2, a length of the pulse-wave signal SM that corresponds to one heartbeat-synchronous pulse of the cuff pulse wave $W_C$. If a negative judgment is made at SA3, SA3 is repeated while the control device 28 receives the pulse-wave signal SM continuously supplied from the pulse-wave filter circuit 24. Meanwhile, if a positive judgment is made at SA3, the control goes to SA4, corresponding to the pulse-wave-peak determining means 52, where the control device 28 determines, according to a well-known data-process technique, a peak point of the one heartbeat-synchronous pulse of the cuff pulse wave We that has been received while SA3 is repeated.

Next, the control goes to Steps SA5, SA6, and SA7 corresponding to the increase-end-pressure determining means 54. First, at SA5, the control device 28 determines a rate V of decrease of a portion of the one pulse that starts with the peak point determined at SA4 and lasts for a prescribed time duration $T_1$ (e.g., half a time duration between the peak point and the rising point of another pulse following the one pulse). Supposing that t(1) is a time of detection of the peak point of the one pulse, A(1) is a magnitude of the peak point of the one pulse, t(2) is a time after the prescribed time duration $T_1$, and A(2) is a magnitude of the one pulse at the time t(2), the decrease rate V is expressed as follows:

$$V=-\{A(2)-A(1)\}/\{t(1)\} \qquad (1)$$

Then, at SA6, the control device 28 judges whether the decrease rate V determined at SA5 is greater than a prescribed reference value $V_{SET}$. If a negative judgment is made at SA6, Step SA3 and the following steps are repeated, so that the quick cuff inflation is continued, new heartbeat-synchronous pulses of the cuff pulse wave $W_C$ are detected, and respective decrease rates V of the new pulses are determined.

Meanwhile, if a positive judgment is made at SA6, it indicates that the static pressure $P_C$ at the time of detection of one pulse whose decrease rate V is judged to be greater than the reference value $V_{SET}$ is substantially equal to a systolic blood pressure $BP_{SYS}$ of the subject. Then, at SA7, the control device 28 adds a prescribed addition value α (e.g., 20 mmHg) to the static pressure $P_C$ at that time, and thereby determines an increase-end pressure $P_{CE}$.

At SA8, the control device 28 judges whether the current static pressure $P_C$ is higher than the increase-end pressure $P_{CE}$ determined at SA7. If a negative judgment is made at SA8, SA7 is repeated, so that the quick increasing of the static pressure $P_C$ is continued. Meanwhile, if a positive judgment is made at SA8, then the control goes to SA9 to stop the air pump 18 and thereby end the quick cuff inflation.

At SA10, the control device 28 switches the pressure control valve 16 to its slow-deflation position, so that the slow decreasing of the static pressure $P_C$ is started. Then, the control goes to Steps SA11 and SA12 corresponding to the blood-pressure determining means 56. First, at SA11, the control device 28 determines, based on the change of respective amplitudes of heartbeat-synchronous pulses of the cuff pulse wave $W_C$ continuously detected during the slow decreasing of the static pressure $P_C$, a systolic blood pressure $BP_{SYS}$, a mean blood pressure $BP_{MEAN}$, and a diastolic blood pressure $BP_{DIA}$ of the subject, according to the well-known oscillometric algorithm.

Since the diastolic blood pressure $BP_{DIA}$ is last determined according to the oscillometric algorithm, the control device 28 judges, at SA12, whether the diastolic blood pressure $BP_{DIA}$ has been determined, and thereby determines whether the current blood-pressure measuring operation has been finished. If a negative judgment is made at SA12, Steps SA11 and SA12 are repeated. Meanwhile, if a positive judgment is made at SA12, then the control goes to SA13 to switch the pressure control valve 16 to its quick-deflation position and thereby quickly release the static pressure $P_C$. And, at SA14, the control device 28 operates the display device 40 to display the blood-pressure values BP determined at SA11. In the flow chart shown in FIG. 4, Steps SA2, SA9, SA10, and SA13 correspond to the cuff-pressure changing means 50.

Figure 4:
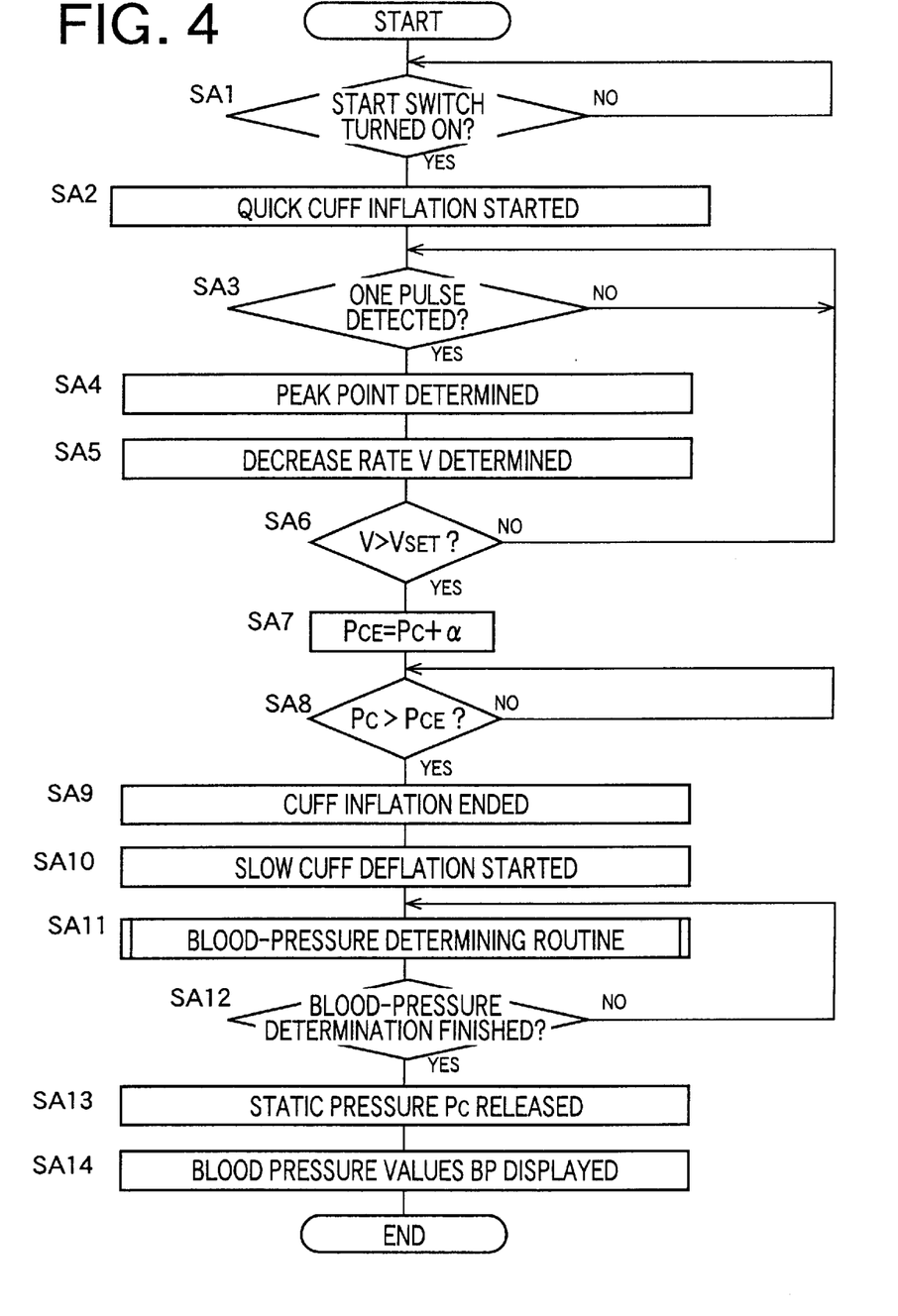
FIG. 4 is a flow chart representing a control program according to which the control device shown in FIG. 1 is operated.

It emerges, from the foregoing description of the illustrated embodiment employing the flow chart shown in FIG. 4, that at Steps SA5 to SA7 (i.e., the increase-end-pressure determining means 54), the increase-end pressure $P_{CE}$ at which the quick increasing of the static pressure $P_C$ is to be ended is determined based on the fact that the decrease rate V of one pulse (i.e., a portion of the one pulse from its peak point to the end of the prescribed time duration $T_1$) of the cuff pulse wave $W_C$ detected during the quick increasing of the static pressure $P_C$, is greater than the prescribed reference value $V_{SET}$. Thus, the quick increasing of the static pressure $P_C$ of the cuff 12 is ended at the thus determined increase-end pressure $P_{CE}$ that is the most suitable for the individual subject whose systolic blood pressure $BP_{SYS}$ may differ from those of other subjects.

Figure 5:
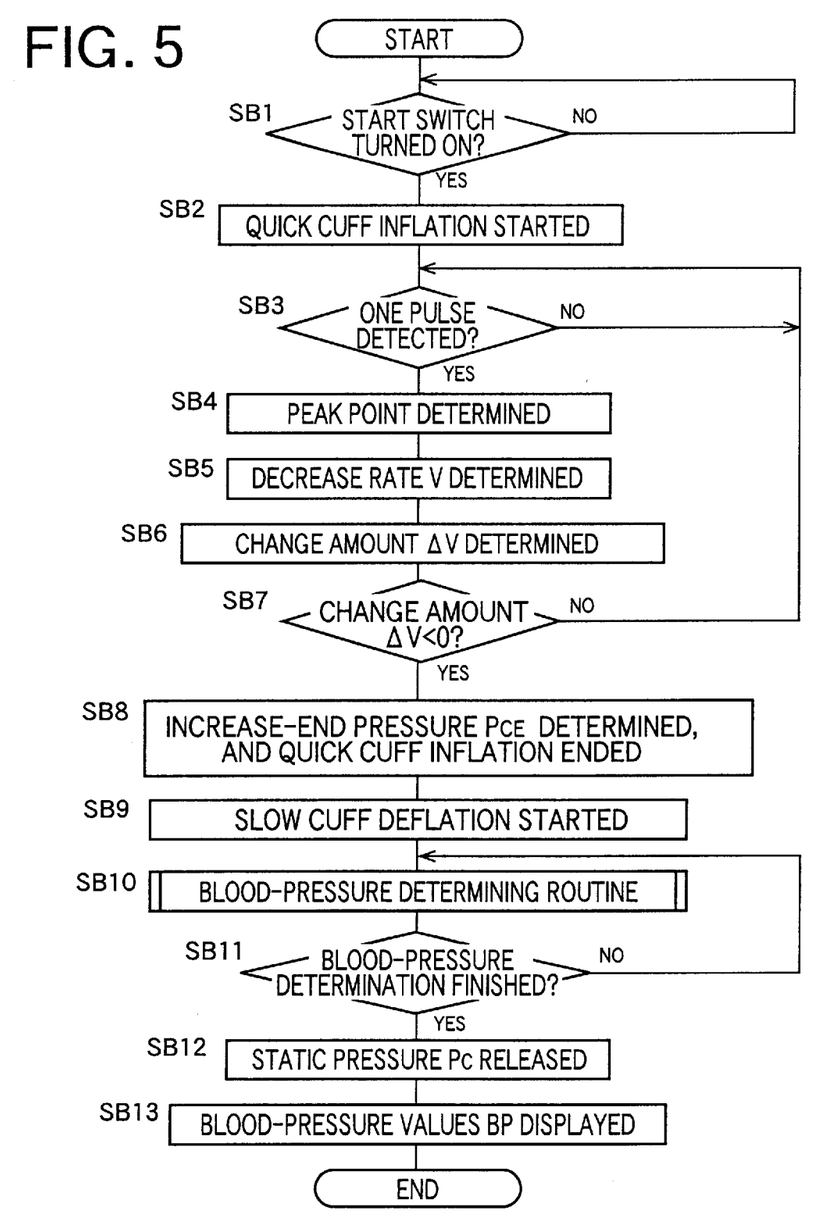
FIG. 5 is another flow chart representing another control program according to which the control device shown in FIG. 1 is operated.

FIG. 5 shows another flow chart that is different from the flow chart shown in FIG. 4 and represents another control program according to which the control device 28 shown in FIG. 1 may be operated.

In the flow chart of FIG. 5, Steps SB1 to SB5 are the same as Steps SA1 to SA5 of the flow chart of FIG. 4. Then, at SB6, the control device 28 determines an amount $\Delta V$ of change of a decrease rate $V_n$ (n is an ordinal number counted from the commencement of the quick cuff inflation) of one heartbeat-synchronous pulse of the cuff pulse wave $W_C$, determined at SB5, from a decrease rate $V_{n-1}$ of another pulse preceding the one pulse, according to the following expression (2):

$$\Delta V = V_n - V_{n-1} \qquad (2)$$

At SB7, the control device 28 judges whether the change amount $\Delta V$ determined at SB6 is smaller than zero. Under the condition that the static pressure $P_C$ is lower than the systolic blood pressure $BP_{SYS}$ of the subject, the respective decrease rates V of the respective heartbeat-synchronous pulses increase as the static pressure $P_C$ increases, and accordingly the each of the respective change amounts $\Delta V$ of the respective pulses is greater than zero. Thus, under this condition, a negative judgment is made at SB7. In this case, Step SB3 and the following steps are repeated, so that the quick increasing of the static pressure $P_C$ is continued.

On the other hand, if the static pressure $P_C$ exceeds the systolic blood pressure $BP_{SYS}$ of the subject, the respective decrease rates V of the pulses significantly decrease, and accordingly a change amount $\Delta V$ of the decrease rate $V_n$ of one pulse detected immediately after the static pressure $P_C$ exceeds the systolic blood pressure $BP_{SYS}$, from the decrease rate $V_{n-1}$ of the preceding pulse is smaller than zero. Thus, if the static pressure PC exceeds the systolic blood pressure $BP_{SYS}$ of the subject, a positive judgment is made at SB7.

If a positive judgment is made at SB7, then control goes to SB8 to determine, as an increase-end pressure $P_{CE}$, the current static pressure $P_C$ at that time, and simultaneously stop the operation of the air pump 18. Step SB9 and the following steps are the same as Step SA10 and the following steps of the flow chart of FIG. 4. Eventually, the control device 28 determines blood-pressure values BP of the subject. In this flow chart, Steps SB5 to SB8 correspond to the increase-end-pressure determining means 54.

From the foregoing description of the illustrated embodiment employing the flow chart shown in FIG. 5, it is apparent that at Steps SB5 to SB8 (the increase-end-pressure determining means 54), the increase-end pressure $P_{CE}$ at which the quick increasing of the static pressure $P_C$ is to be ended is determined based on the fact that the change amount $\Delta V$ of the decrease rate V of one pulse (i.e., a portion of the one pulse from its peak point to the end of the prescribed time duration $T_1$) of the cuff pulse wave $W_C$ detected during the quick increasing of the static pressure $P_C$, is smaller than zero. Thus, the quick increasing of the static pressure $P_C$ of the cuff 12 is ended at the thus determined increase-end pressure $P_{CE}$ that is the most suitable for the individual subject whose systolic blood pressure $BP_{SYS}$ may differ from those of other subjects.

Figure 6:
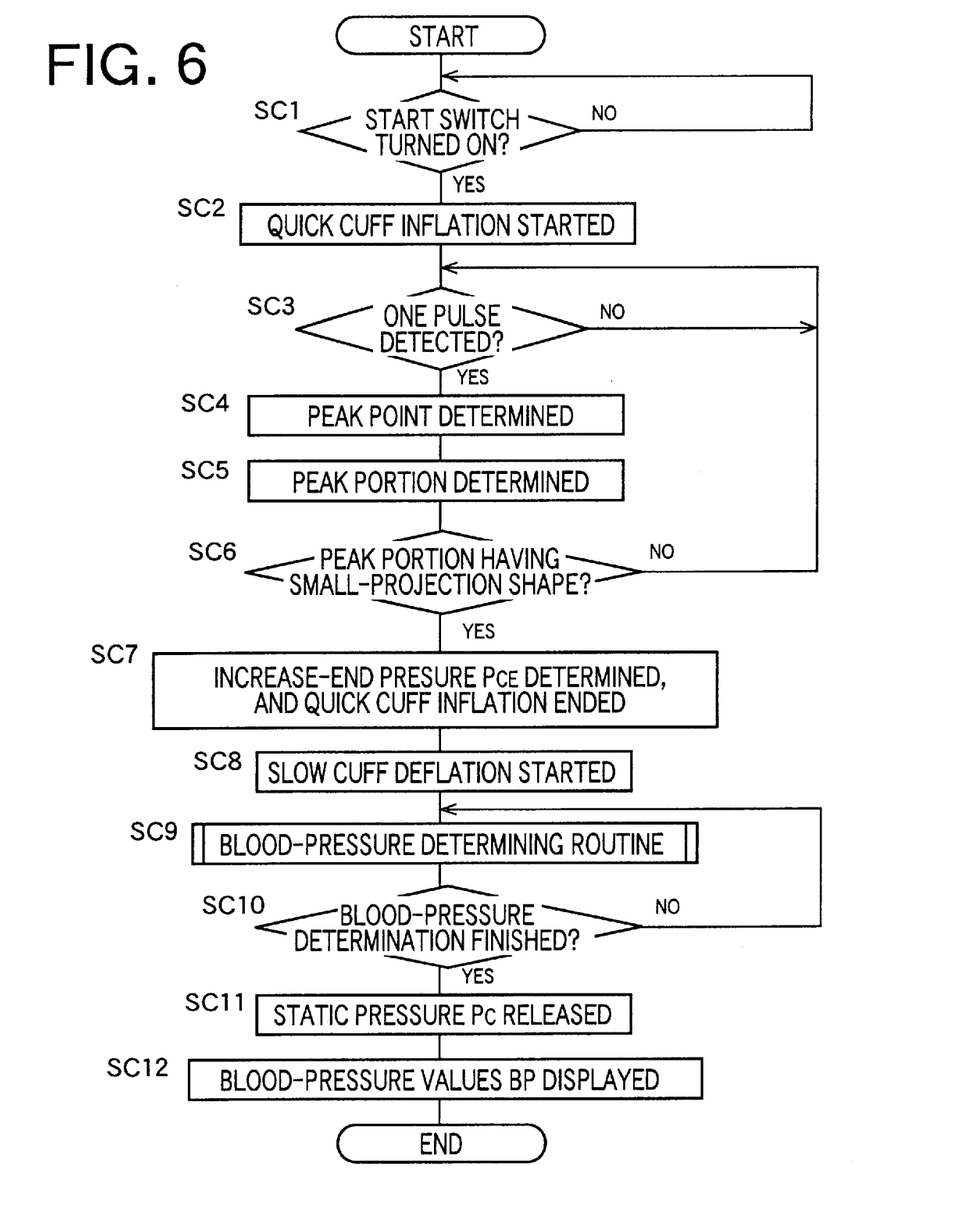
FIG. 6 is yet another flow chart representing yet another control program according to which the control device shown in FIG. 1 is operated.

FIG. 6 shows yet another flow chart that is different from the flow charts shown in FIGS. 4 and 5 and represents yet another control program according to which the control device 28 shown in FIG. 1 may be operated.

In the flow chart of FIG. 6, Steps SC1 to SC4 are the same as Steps SA1 to SA4 of the flow chart of FIG. 4. Then, at SC5, the control device 28 determines, as a peak portion of one heartbeat-synchronous pulse of the cuff pulse wave $W_C$, read in at SC3, a middle portion of the one pulse that has, as the center of the middle portion, the peak point of the one pulse determined at SC4 and has a length equal to half an entire length of the one pulse.

At SC6, the control device 28 judges whether the peak portion of the one pulse, determined at SC5, has a small-projection shape. In the case where the peak portion of the one pulse has the small-projection shape, the peak portion has, before its peak point, a first deflection point where the rate of increase of the magnitude of the peak portion significantly largely increases and accordingly is greater than a prescribed increase-ate value, and has, after the peak point, a second deflection point where the rate of decrease of the magnitude of the peak portion significantly largely decreases and accordingly is smaller than a prescribed decrease-rate value. Therefore, at SC6, the control device 28 judges whether the peak portion includes both the first and second deflation points.

Under the condition that the static pressure $P_C$ is lower than the systolic blood pressure $BP_{SYS}$ of the subject, each of the respective peak portions of the respective heartbeat-synchronous pulses does not have the small-projection shape, and accordingly a negative judgment is made at SC6. In this case, Step SC3 and the following steps are repeated, so that the quick increasing of the static pressure $P_C$ is continued.

On the other hand, if the static pressure $P_C$ exceeds the systolic blood pressure $BP_{SYS}$ of the subject, each of the respective peak portions of the pulses shows the small-projection shape, and accordingly a positive judgment is made at SC6. If a positive judgment is made at SC6, then control goes to SC7 to determine, as an increase-end pressure $P_{CE}$, the current static pressure $P_C$ at that time, and simultaneously stop the operation of the air pump 18. Step SC8 and the following steps are the same as Step SA10 and the following steps of the flow chart of FIG. 4. Eventually, the control device 28 determines blood-pressure values BP of the subject. In this flow chart, Steps SC5 to SC7 correspond to the increase-end-pressure determining means 54.

From the foregoing description of the illustrated embodiment employing the flow chart shown in FIG. 6, it is apparent that at Steps SC5 to SC7 (the increase-end-pressure determining means 54), the increase-end pressure $P_{CE}$ at which the quick increasing of the static pressure $P_C$ is to be ended is determined based on the fact that the peak portion of one pulse of the cuff pulse wave $W_C$, detected during the quick increasing of the static pressure $P_C$, has the small-projection shape. Thus, the quick increasing of the static pressure $P_C$ of the cuff 12 is ended at the thus determined increase-end pressure $P_{CE}$ that is the most suitable for the individual subject whose systolic blood pressure $BP_{SYS}$ may differ from those of other subjects.

While the present invention has been described in its preferred embodiments by reference to the drawings, it is to be understood that the invention may otherwise be embodied.

For example, the illustrated automatic blood-pressure measuring apparatus 10 employs the oscillometric blood-pressure measuring method. However, the apparatus 10 may employ so-called Korotkoff-sound method in which blood-pressure values are determined based on respective values of a cuff pressure when Korotkoff sounds are first and last detected. Otherwise, the apparatus 10 may employ a supersonic Doppler method in which supersonic transmitter and receiver are placed right above an artery to detect the opening and closing of the artery when the pressing force applied to the artery is changed, and thereby determine a blood pressure.

It is to be understood that the present invention may be embodied with other changes, improvements, and modifications that may occur to a person skilled in the art without departing from the spirit and scope of the invention defined in the appended claims.

What is claimed is:

1. An apparatus for automatically measuring a blood pressure of a living subject, comprising:
    an inflatable cuff which is adapted to be wound around a portion of the subject;
    an increase-end-pressure determining means for determining, based on a cuff pulse wave occurring to the cuff when a pressure in the cuff is increased at a first rate, an increase-end pressure to which the pressure of the cuff is increased at the first rate, at which the increasing of the pressure of the cuff is ended, and from which the pressure of the cuff is decreased at a second rate lower than the first rate; and
    a blood-pressure determining means for determining a blood pressure of the subject based on a physical signal obtained from the subject when the pressure of the cuff is decreased at the second rate from the increase-end pressure,
    wherein the increase-end-pressure determining means determines the increase-end-pressure based on a rate of decrease of an after-peak-point portion of at least one heartbeat-synchronous pulse of the cuff pulse wave occurring to the cuff when the pressure of the cuff is increased at the first rate, said after-peak-point portion starting with a peak point of said heartbeat-synchronous pulse.

2. An apparatus according to claim 1, further comprising:
    a pressure sensor which detects the pressure in the cuff; and
    a cuff-pressure changing device which increases the pressure of the cuff at the first rate and decreases the pressure of the cuff at the second rate lower than the first rate.

3. An apparatus according to claim 1, wherein the blood-pressure determining means determines the blood pressure of the subject based on the physical signal comprising the cuff pulse wave occurring to the cuff when the pressure of the cuff is decreased at the second rate from the increase-end pressure.

4. An apparatus according to claim 1, further comprising a display device which displays the blood pressure determined by the blood-pressure determining means.

5. An apparatus for automatically measuring a blood pressure of a living subject comprising:
    an inflatable cuff which is adapted to be wound around a portion of the subject;
    a cuff-pulse-wave detecting device which detects cuff pulse wave occurring to the cuff when the pressure of the cuff is increased at first rate;
    an increase-end-pressure determining means for determining, based on the cuff pulse wave occurring to the cuff, when a pressure in the cuff is increased at the first rate, an increase-end pressure to which the pressure of the cuff is increased at the first rate, at which the increasing of the pressure of the cuff is ended, and from which the pressure of the cuff is decreased at a second rate lower than the first rate; and
    a blood-pressure determining means for determining a blood pressure of the subject based on a physical signal obtained from the subject when the pressure of the cuff is decreased at the second rate from the increase-end pressure,
    wherein the increase-end-pressure determining means includes:
        a peak-point identifying means for identifying a peak point of at least one heartbeat-synchronous pulse of the detected cuff pulse wave;
        a decrease-rate determining means for determining a rate of decrease of an after-peak-point portion of said heartbeat-synchronous pulse that starts with the identified peak point of the heartbeat-synchronous pulse and lasts in a predetermined time duration after the peak point;
        a judging means for judging whether the determined rate of decrease of the after-peak-point portion of said heartbeat-synchronous pulse is greater than a prescribed decrease-rate value; and
        means for determining the increase-end pressure based on a pressure of the cuff at a time when said heartbeat-synchronous pulse, for which said determined rate of decrease is judged as being greater than the prescribed decrease-rate value, is detected by the cuff-pulse-wave detecting device.

6. An apparatus for automatically measuring a blood pressure of a living subject comprising:
    an inflatable cuff which is adapted to be wound around a portion of the subject;
    a cuff-pulse-wave detecting device which detects a cuff pulse wave occurring to the cuff when the pressure of the cuff is increased at a first rate;

an increase-end pressure determining means for determining, based on the cuff pulse wave occurring to the cuff when a pressure in the cuff is increased at the first rate, an increase-end-pressure to which the pressure of the cuff is increased at the first rate at which the increasing of the pressure of the cuff is ended, and from which the pressure of the cuff is decreased at a second rate lower than the first rate; and a blood-pressure determining means for determining a blood pressure of the subject based on a physical signal obtained from the subject when the pressure of the cuff is decreased at the second rate from the increase-end pressure, wherein the increase-end-pressure determining means includes:

a peak-point identifying means for identifying a peak point of each of plurality of heartbeat-synchronous pulses of the detected cuff pulse wave;

a decrease-rate determining means for determining a rate of decrease of an after-peak-point portion of said each of the heartbeat-synchronous pulses that starts with the identified peak point of said each heartbeat-synchronous pulse and lasts in a predetermined time duration after the peak point;

a change-amount determining means for determining an amount of change of the determined rate of decrease of the after-peak-point portion of said each heartbeat-synchronous pulse from the determined rate of decrease of the after-peak-point portion of a heartbeat-synchronous pulse prior to said each heartbeat-synchronous pulse;

a judging means for judging whether the determined amount of change of the determined rate of decrease of the after-peak-point portion of said each heartbeat-synchronous pulse is smaller than zero; and means for determining the increase-end pressure based on a pressure of the cuff at a time when said each heartbeat-synchronous pulse, for which said determined amount of change is judged as being smaller than zero, is detected by the cuff-pulse-wave detecting device.

7. An apparatus for automatically measuring a blood pressure of a living subject, comprising:

an inflatable cuff which is adapted to be wound around a portion of the subject;

a cuff-pulse-wave detecting device which detects at least one heartbeat-synchronous pulse of cuff pulse wave occurring to the cuff when the pressure of the cuff is increased at first rate;

an increase-end-pressure determining means for determining, based on whether a peak portion of said at least one heartbeat-synchronous pulse of the cuff pulse wave occurring to the cuff when a pressure in the cuff is increased at the first rate has a small-projection shape, an increase-end pressure to which the pressure of the cuff is increased at the first rate, at which the increasing of the pressure of the cuff is ended, and from which the pressure of the cuff is decreased at a second rate lower than the first rate; and a blood-pressure determining means for determining a blood pressure of the subject based on a physical signal obtained from the subject when the pressure of the cuff is decreased at the second rate from the increase-end pressure, wherein the increase-end-pressure determining means further includes:

a peak-point identifying means for identifying a peak point of said heartbeat-synchronous pulse of the cuff pulse wave;

a peak-portion determining means for determining, as the peak portion of said heartbeat-synchronous pulse, a portion of the heartbeat-synchronous pulse that has, as a center thereof, the identified peak point of the heartbeat-synchronous pulse and has a predetermined length shorter than an entire length of the heartbeat-synchronous pulse;

a small-projection-shape identifying means for identifying the small-projection shape of the peak portion by judging that the peak portion has, before the peak point, a first deflection point where a rate of increase of the peak portion significantly largely increases and accordingly is greater than a prescribed increase-rate value, and has, after the peak point, a second deflection point where a rate of decrease of the peak portion significantly largely decreases and accordingly is smaller than a prescribed decrease-rate value; and means for determining the increase-end pressure based on a pressure of the cuff at a time when said heartbeat-synchronous pulse, for which said small-projection shape of the peak portion is identified, is detected by the cuff-pulse-wave detecting device.

* * * * *